US008835698B2

(12) United States Patent
Johnson et al.

(10) Patent No.: US 8,835,698 B2
(45) Date of Patent: *Sep. 16, 2014

(54) METHOD FOR PRODUCING FLUORINATED ORGANIC COMPOUNDS

(71) Applicant: Honeywell International Inc., Morristown, NJ (US)

(72) Inventors: Robert C. Johnson, Lancaster, NY (US); Hsueh S. Tung, Getzville, NY (US); Daniel C. Merkel, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/888,443

(22) Filed: May 7, 2013

(65) Prior Publication Data
US 2013/0253235 A1    Sep. 26, 2013

Related U.S. Application Data

(60) Continuation of application No. 13/287,199, filed on Nov. 2, 2011, now Pat. No. 8,455,704, which is a division of application No. 12/185,042, filed on Aug. 1, 2008, now Pat. No. 8,071,825, said application No. 13/287,199 is a continuation-in-part of application No. 11/619,592, filed on Jan. 3, 2007, now Pat. No. 8,084,653.

(60) Provisional application No. 60/953,528, filed on Aug. 2, 2007, provisional application No. 60/755,485, filed on Jan. 3, 2006.

(51) Int. Cl.
C07C 17/00    (2006.01)

(52) U.S. Cl.
USPC ............................ 570/157; 570/155; 570/156

(58) Field of Classification Search
USPC .......................................... 570/157, 156, 155
See application file for complete search history.

(56) References Cited

U.S. PATENT DOCUMENTS

| | | | |
|---|---|---|---|
| 2,931,840 | A | 4/1960 | Marquis |
| 4,900,874 | A | 2/1990 | Ihara et al. |
| 7,678,949 | B2 | 3/2010 | Rao et al. |
| 2005/0245773 | A1 | 11/2005 | Mukhopadhyay et al. |
| 2007/0197842 | A1 | 8/2007 | Mukhopadhyay et al. |
| 2008/0207963 | A1 | 8/2008 | Rao et al. |

FOREIGN PATENT DOCUMENTS

WO    2007079431 A2    7/2007

OTHER PUBLICATIONS

Banks et al., Preparation of 2,3,3,3-Tetrafluoropropene From Trifluoroacetylacetone and Sulphur Tetrafluoride, Journal of Fluorine Chemistry, pp. 171-174, vol. 82 (1997) GB.

Primary Examiner — Jafar Parsa
(74) Attorney, Agent, or Firm — Bruce O. Bradford

(57) ABSTRACT

Disclosed are processes for the production of fluorinated olefins, preferably adapted to commercialization of $CF_3CF=CH_2$ (1234yf). In certain preferred embodiments the processes comprise first exposing a compound of Formula (IA)

$$C(X)_2=CClC(X)_3 \qquad (IA)$$

where each X is independently F, Cl or H, preferably $CCl_2=CClCH_2Cl$, to one or more sets of reaction conditions, but preferably a substantially single set of reaction conditions, effective to produce at least one chlorofluoropropane, preferably in accordance with Formula (IB):

$$CF_3CClX'C(X')_3 \qquad \text{Formula (IB)}$$

where each X' is independently F, Cl or H, and then exposing the compound of Formula (IB) to one or more sets of reaction conditions, but preferably a substantially single set of reaction conditions, effective to produce a compound of Formula (II)

$$CF_3CF=CHZ \qquad (II)$$

where Z is H, F, Cl, I or Br.

16 Claims, 1 Drawing Sheet

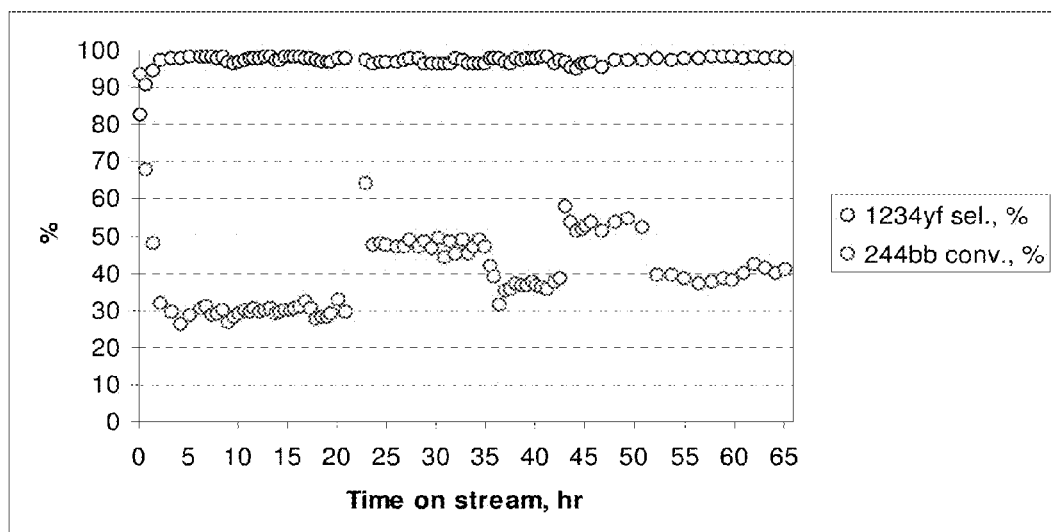
Conditions: Feed 95GC% 244bb/3.1GC% 1233xf/ 0.35GC% 245cb; 2.0 L of 10wt% CsCl/90 wt% $MgF_2$ catalyst; 1.0 lb/hr feed rate.

METHOD FOR PRODUCING FLUORINATED ORGANIC COMPOUNDS

CROSS-REFERENCES TO RELATED APPLICATIONS

This application is a Continuation of U.S. application Ser. No. 13/287,199, filed on Nov. 2, 2011 (now U.S. Pat. No. 8,455,704), which in turn is a Divisional of U.S. application Ser. No. 12/185,042, filed on Aug. 1, 2008 (now U.S. Pat. No. 8,071,825), which claims priority benefit of U.S. Provisional Application No. 60/953,528, filed on Aug. 2, 2007, which in turn is also a Continuation-In-Part of U.S. application Ser. No. 11/619,592, filed Jan. 3, 2007 (now U.S. Pat. No. 8,084,653), which claims priority benefit of U.S. Provisional Application No. 60/755,485, filed Jan. 3, 2006, each of which are incorporated herein by reference.

BACKGROUND OF THE INVENTION (1) Field of Invention

This invention relates to novel methods for preparing fluorinated organic compounds, and more particularly to methods of producing fluorinated olefins having a fluorine on an unsaturated non-terminal carbon.

(2) Description of Related Art

Hydrofluorocarbons (HFCs), in particular hydrofluoroalkenes such as tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and, thus, pose no threat to the ozone layer.

Several methods of preparing hydrofluoroalkenes are known. For example, U.S. Pat. No. 4,900,874 (Ihara, et. al) describes a method of making fluorine containing olefins by contacting hydrogen gas with fluorinated alcohols. Although this appears to be a relatively high-yield process, commercial handling of hydrogen gas at high temperature is generally unsafe. Also, the cost of producing hydrogen gas, such as building an on-site hydrogen plant, can be, in many situations, prohibitive.

U.S. Pat. No. 2,931,840 (Marquis) describes a method of making fluorine containing olefins by pyrolysis of methyl chloride and tetrafluoroethylene or chlorodifluoromethane. This process produces a relatively low yield and a very large percentage of unwanted and/or unimportant byproducts.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

SUMMARY OF INVENTION

One aspect of the invention involves methods of producing hydrofluoroalkenes, more preferably fluorinated olefins having a fluorine on an unsaturated non-terminal carbon and even more preferably in certain preferred embodiments 2,3,3,3-tetrafluoro-1-propene (HFO-1234yf). In preferred forms, this aspect of the invention is directed to methods comprising converting at least one compound of Formula (I):

$$C(X)_m CCl(Y)_n C(X)_m \tag{I}$$

to at least one compound of Formula (II)

$$CF_3 CF = CHZ \tag{II}$$

where each X, Y and Z is independently H, F, Cl, I or Br, and each m is independently 1, 2 or 3, preferably 2 or 3, and n is 0 or 1. In certain preferred embodiments, compounds of Formula I include $CH_2=CClCCl_3$, $CCl_2=CClCH_2Cl$, and 1,1,1,2,3-pentachloropropane. As used herein and throughout, unless specifically indicated otherwise, the term "converting" includes directly converting (for example, in a single reaction or under essentially one set of reaction conditions) and indirectly converting (for example, through two or more reactions or using more than a single set of reaction conditions).

In certain preferred embodiments of the invention, the compound of Formula (I) comprises a compound wherein n is 0, each X is independently H or Cl, and Z is H. Such preferred embodiments include converting at least one C3 alkene in accordance with Formula (IA):

$$C(X)_2 = CClC(X)_3 \tag{IA}$$

to at least one compound of formula (II)

$$CF_3 CF = CHZ \tag{II}$$

where each X is independently H or Cl. Preferably the one or more compounds of Formula (IA) are tetrachloropropene(s), and are even more preferably selected from the group consisting of $CH_2=CClCCl_3$, $CCl_2=CClCH_2Cl$, and combinations of these. In certain highly preferred embodiments, the at least one C3 alkene in accordance with Formula (IA) comprises, and preferably comprises in a major proportion based on all compounds of Formula (I), $CCl_2=CClCH_2Cl$.

In certain preferred embodiments the converting step comprises first exposing the compound of Formula (I), and preferably Formula (IA), and even more preferably $CCl_2=CClCH_2Cl$, to one or more sets of reaction conditions, but preferably a substantially single set of reaction conditions, effective to produce at least one chlorofluoropropane, more preferably a propane in accordance with Formula (IB):

$$CF_3 CClXC(X)_3 \qquad \text{Formula (IB)}$$

where each X is independently F, Cl or H, preferably where one X is F and the remaining X's are H, and then exposing the compound of Formula (IB) to one or more sets of reaction conditions, but preferably a substantially single set of reaction conditions, effective to produce a compound of Formula (II), most preferably HFO-1234yf. In certain preferred embodiments, at least one of said X in Formula (IB) is Cl. In such embodiments, it is generally preferred that X on the non-terminal carbon is H, and even more preferably that in addition that at least two, and more preferably all three X on the terminal carbon are also H.

As used herein, the term "substantially single set of reaction conditions" means that the reaction is controlled to correspond to be within a set of reaction parameters that would ordinarily be considered to be a single stage or unit operation. As those skilled in the art will appreciate, such conditions permit a degree of design variability within each of the process parameters relevant to the conversion step.

The preferred conversion step of the present invention is preferably carried out under conditions, including the use of one or more reactions, effective to provide an overall Formula (I) conversion of at least about 50%, more preferably at least about 75%, and even more preferably at least about 90%. In certain preferred embodiments the overall conversion of Formula (I) is at least about 95%, and more preferably at least about 97%. Further, in certain preferred embodiments, the step of converting the compound of Formula (I) to produce a compound of Formula (II) is conducted under conditions effective to provide an overall Formula (II) yield of at least about 75%, more preferably at least about 85%, and more preferably at least about 90%. In certain preferred embodiments an overall yield of about 95% or greater is achieved.

In the preferred embodiments in which the conversion step comprises exposing a compound of Formula (I), and even more preferably $CCl_2$=$CClCH_2Cl$, to one or more sets of reaction conditions effective to produce at least one chlorofluoropropane, more preferably a propane in accordance with Formula (IB), such an exposing step preferably comprises exposing the compound of Formula (I) to one or more set of reaction conditions, but preferably substantially a single set of reaction conditions, effective to provide an overall conversion of Formula (I), and preferably Formula (IA) of at least about 75%, and more preferably at least about 90%, and more preferably at least about 97%, such conditions also preferably being effective to provide a Formula (IB) selectivity yield of at least about 10%, more preferably at least about 15%, and even more preferably at least about 20%.

One preferred aspect of the present invention provides a process for the production of 2-chloro-1,1,1,2-tetrafluoropropane (HCFC244bb) comprising reacting a compound selected from the group consisting of 1,1,2,3-tetrachloropropene, 1,1,1,2,3-pentachloropropane (HCC-240 db), 2,3,3,3-tetrachloropropene and combinations of these with a fluorinating agent, preferably hydrogen fluoride, in a liquid phase reaction vessel in the presence of a liquid phase fluorination catalyst.

Another preferred aspect of the invention provides a process for the production of 2,3,3,3-tetrafluoropropene comprising (i) reacting, preferably in a continuous process, at least one compound selected from the group consisting of 1,1,2,3-tetrachloropropene, 1,1,1,2,3-pentachloropropane (HCC-240 db), and 2,3,3,3-tetrachloropropene with a fluorinating agent, preferably hydrogen fluoride, in a liquid phase reaction in the presence of a liquid phase fluorination catalyst to produce a reaction product comprising 2-chloro-1,1,1,2-tetrafluoropropane (HCFC-244bb); and then (ii) reacting, preferably by dehydrohalogenating, the 2-chloro-1,1,1,2-tetrafluoropropane (HCFC-244bb) under conditions effective to produce 2,3,3,3-tetrafluoropropene.

BRIEF DESCRIPTION OF THE DRAWINGS

FIG. 1 is a chart showing the yield of HFC-1234yf according to an embodiment of the invention.

DETAILED DESCRIPTION OF PREFERRED EMBODIMENTS

One beneficial aspect of the present invention is that it enables the production of desirable fluoroolefins, preferably C3 fluoroolefins, using relatively high conversion reactions. Furthermore, the present methods in certain preferred embodiments permit the production of the desirable fluoroolefins, either directly or indirectly, from relatively attractive starting materials. For example, tetrachloropropene, and 1,1,2,3 tetrachloropropene ($CCl_2$=$CClCH_2Cl$) in particular, is a compound that in certain embodiments is an advantageous starting material.

In certain preferred embodiments, at least a first compound in accordance with Formula (I), and preferably a compound in accordance with Formula (IA), is exposed to one or more reaction conditions effective to produce a second compound in accordance with Formula (I), and preferably a compound in accordance with Formula (IB), which in turn is exposed to one or more reaction conditions effective to produce a reaction product containing one or more of the desired fluoroolefins, preferably one or more compounds of Formula (II), and even more preferably HFO-1234yf. Thus, in preferred embodiments, the conversion step comprises a series of at least two reaction stages or conditions. In one preferred aspect of the present invention, the conversion step comprises: (a) reacting a compound of Formula (IA), such as tetrachloropropene, preferably in a liquid phase reaction in the presence of at least a first catalyst to produce at least one compound of Formula (IB), such as a monochloro-tetrafluoro-propane, preferably 2-chloro-1,1,1,2-tetrafluoropropane (HFC-244bb); and (b) reacting said compound of Formula (IB), in a gas and/or liquid phase, to produce the desired HFO, preferably HFO-1234yf.

In certain preferred embodiments, the present methods comprise converting at least one tetrachloropropene and/or at least one pentachloropropane to a reaction product containing the desired tetrafluoropropene, preferably 2,3,3,3-tetrafluoropropene (HFO-1234yf). Although it is contemplated that the converting step in certain embodiments may effectively be carried out in a single reaction stage and/or under a single set of reaction conditions, it is preferred in many embodiments that the converting steps comprise a series of two reaction stages or conditions. In one preferred aspect of the present invention, the conversion step comprises: (a) reacting at least one tetrachloropropene (preferably, 1,1,2,3-tetrachloropropene and/or 2,3,3,3-tetrachloropropene), or at least one pentachloropropane (1,1,1,2,3-pentachloropropane) or mixtures of two or more thereof, in a liquid and/or gas phase reaction in the presence of at least a first catalyst to produce at least one C3 hydrochlorofluorocarbon such as a monochloro-tetrafluoro-propane, preferably HCFC-244bb; and (b) reacting said C3 hydrochlorofluorocarbon, such as a monochloro-tetrafluoropropane compound, in a gas and/or liquid phase and preferably in the presence of at least a catalyst, preferably a second catalyst which is different than the first catalyst, to produce the desired tetrafluoropropene, preferably HFO-1234yf.

Each of the preferred reaction steps is described in detail below, with the headings being used for convenience but not necessarily by way of limitation.

I. Fluorination of the Compound of Formula (IA)

One preferred reaction step in accordance with the present invention may be described by those reactions in which the compound of Formula (IA) is fluorinated to produce a compound of Formula (IB). In certain preferred embodiments, especially embodiments in which the compound of Formula (IA) comprises $C(X)_2$=$CClC(X)_3$, where each X is independently H or Cl, the present converting step comprises reacting said Formula (IA) compound(s) by fluorinating, preferably in a liquid phase and with HF as a fluorinating agent, said compound(s) to produce a compound of Formula (IB), namely,

   Formula (IB)

where each X' is independently F, Cl or H. The preferred fluorination of the compound of Formula (IA) is preferably carried out under conditions effective to provide a Formula (IA) conversion of at least about 50%, more preferably at least about 75%, and even more preferably at least about 90%. In certain preferred embodiments the conversion is at least about 95%, and more preferably at least about 97%. Further, in certain preferred embodiments, the conversion of the compound of Formula (IA) comprises reacting such compound under conditions effective to produce at least one compound of Formula (IB), such as monochlorotetrafluoropropane (preferably HCFC-244bb) at a selectivity of at least about 10%, more preferably at least about 15%, and more preferably at least about 20%.

In certain preferred embodiments in which the feed material comprises tetrachloropropene, the present converting step is carried out under conditions effective to provide a tetrachloropropene conversion of at least about 40%, more preferably at least about 55%, and even more preferably at least about 70%. In certain preferred embodiments the conversion of tetrachloropropene is at least about 90%, and more preferably about 100%. Further, in certain preferred embodiments, the conversion of the tetrachloropropene to produce a C3 hydrochlorofluorocarbon is conducted under conditions effective to provide a C3 hydrochlorofluorocarbon selectivity of at least about 85%, more preferably at least about 90%, and more preferably at least about 95%, and even more preferably about 100%.

In a particularly preferred embodiment, the invention relates to a continuous method for producing a compound of Formula (IB), preferably including 2-chloro-1,1,1,2-tetrafluoropropane (HCFC-244bb), by either a liquid phase fluorination, a vapor phase fluorination, or a combination of liquid and vapor phase fluorinations. In certain preferred embodiments, the feed to the fluorination reaction comprises at least one chlorocarbon or mixed chlorocarbon feed material, preferably selected from the group consisting of 1,1,1,2,3-pentachloropropane (HCC-240 db), 2,3,3,3-tetrachloropropene, and 1,1,2,3-tetrachloropropene (HCC-1230xa. The compounds in the feed are reacted with a fluorinating agent, such as hydrogen fluoride, to produce a reaction product stream comprising a compound according to Formula (IB), such as 2-chloro-1,1,1,2-tetrafluoropropane, hydrogen fluoride, and hydrogen chloride.

In certain embodiments, it is preferred that the fluorination reaction step is carried out in the liquid phase, and preferably under a substantially single set of reaction conditions, and it is contemplated that the reaction can be carried out batch wise, continuous, or a combination of these, with continuous reaction being preferred. In a preferred form of a continuous process, the Formula (I) compound, such as 1,1,2,3-tetrachloropropene, and the fluorinating agent, such as HF, are preferably fed, preferably substantially simultaneously, to the reactor after the reactor reaches the desired temperature. The temperature and pressure of the fluorination reaction are generally within about the same range for both the batch and continuous modes of operation.

For embodiments in which the reaction comprises a liquid phase reaction, preferably a catalytic process is used. In general, it is contemplated that any liquid phase fluorination catalyst may be used. Lewis acid catalyst, metal-halide catalysts, including antimony halides, tin halides, tantalum halides, titanium halides, transition metal-halides, such as iron halides, niobium halide, and molybdenum halide, transition metal oxides, Group IVb metal halides, a Group Vb metal halides, fluorinated chrome halide, a fluorinated chrome oxide and combinations of two or more of these, are preferred in certain embodiments. Metal chlorides and metal fluorides are particularly preferred. Examples of particularly preferred catalysts of this type include $SbCl_5$, $SbCl_3$, $SbF_5$, $SnCl_4$, $TaCl_5$, $NbCl_5$, $MoCl_6$, $TiCl_4$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, and combinations of two or more of these. Pentavalent metal halide, particularly pentavalent antimony halides are preferred in many embodiments. Antimony chlorides, such as antimony pentachloride, and/or fluorinated antimony chlorides are preferred in many embodiments.

In certain preferred embodiments, a liquid phase catalyst as described above is charged into a fluorination reactor prior to heating the reactor. The catalyst may (or may not) be activated with anhydrous hydrogen fluoride HF (hydrogen fluoride gas) and/or $Cl_2$ (chlorine gas) before use depending on the state of the catalyst.

In preferred liquid phase fluorination of Formula (I) compounds, preferably Formula (IA) compounds, the reaction is at least partially a catalyzed reaction, and is preferably carried out on a continuous basis by introducing a stream containing the compound of Formula (I), preferably Formula (IA), into one or more reaction vessels. The stream containing the compound of Formula (I), and preferably Formula (IA), which may be preheated if desired, is introduced into a reaction vessel, which is maintained at the desired temperature, preferably from about 30° C. to about 200° C., more preferably from about 50° C. to about 150° C., more preferably from about 75° C. to about 125° C., even more preferably in certain embodiments from about 90° C. to about 110° C., wherein it is preferably contacted with catalyst and fluorinating agent, such as HF.

It is generally preferred that the fluorinating agent is present in the reactor in substantial excess. For example, for embodiments in which the fluorinating agent is HF, it is preferred that the reactor be fed with HF in an amount to produce an HF:Formula (IB) ratio in the reactor product stream (on a molar basis) of at least about 4:1, more preferably from about 4:1 to about 50:1, more preferably from about 4:1 to about 30:1 and most preferably from about 5:1 to about 20:1.

With respect to the feeds to the reactor, including the fluorination agent, it is generally considered that water will react with and deactivate the catalyst. Therefore it is preferred that the feed be substantially free of water. With respect to embodiments in which HF is used as a fluorinating agent, substantially anhydrous HF is preferred. By "substantially anhydrous" is meant that the HF contains less than about 0.05 weight % water and preferably contains less than about 0.02 weight % water. However, one of ordinary skill in the art will appreciate that the presence of water in the catalyst can be compensated for by increasing the amount of catalyst used. HF suitable for use in the reaction may be purchased from Honeywell International Inc. of Morristown, N.J.

Although it is contemplated that residence times in the reactor may vary widely within the scope of the present invention, it is preferred in certain embodiments that for continuous reactions the residence time is relatively short. The residence time or contact time in certain preferred embodiments is from about 1 second to about 2 hours, preferably from about 5 seconds to about 1 hour and most preferably from about 10 seconds to about 30 minutes. The quantity of catalyst is generally selected to ensure that the desired level of fluorination is achieved in view of the other process conditions which apply, such as the residence times described above. For example, less than about 5 seconds, more preferably less than about 3 seconds, and even more preferably about 2 seconds or less.

Without necessarily being bound to any particular theory of operation it is believed that the preferred fluorination reaction proceedings in accordance with the following reaction equation:

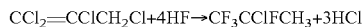

It is expected that by-products of the reaction will include $CF_3CCl=CH_2$ (HFO-1233xf), $CClF_2CCl=CH_2$ (HFO-1232xf), and that one or both of these could be recycled, completely or partially, to improve the overall yield of the desired $CF_3CClFCH_3$ (HCFC-244bb).

In general, it is contemplated that any reactor suitable for a fluorination reaction may be used in accordance with the preferred aspects of the present invention. Preferably the vessel is comprised of materials which are resistant to corrosion as Hastelloy, Inconel, Monel and/or fluoropolymer-lined. Such liquid phase fluorination reactors are well known in the art.

Preferably in certain embodiments, the vessel contains catalyst, for example a fixed or fluid catalyst bed, packed with a suitable fluorination catalyst, with suitable means to ensure that the reaction mixture is maintained with the desired reaction temperature range.

In general it is also contemplated that a wide variety of reaction pressures may be used for the fluorination reaction, depending again on relevant factors such as the specific catalyst being used, the temperature of the reaction, the amount of fluorinating agent being used, and other factors. The reaction pressure can be, for example, superatmospheric, atmospheric or under vacuum and in certain preferred embodiments is from about 5 to about 200 psia, and in certain embodiments from about 30 to about 175 psia and most preferably about 60 psia to about 150 psia.

In certain embodiments, an inert diluent gas, such as nitrogen, may be used in combination with the other reactor feed(s).

It is contemplated that the amount of catalyst used will vary depending on the particular parameters present in each embodiment. In certain preferred embodiments, the catalyst is present in an amount of from about 2% to about 80%, and preferably from about 5% to about 50%, and most preferably from about 10% to about 20%, based on the mole percent of the desired reaction product, preferably a compound in accordance with formula (IB), and even more preferably HCFC-244bb. Fluorination catalysts having a purity of at least 98% are preferred.

The catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

In another embodiment, the fluorination reaction is done in the vapor-phase. In preferred aspects of the vapor phase reaction, the fluorinating agent, such as HF (hydrogen fluoride gas) is fed continuously through the catalyst bed. After a short time with substantially only the HF feed stream, a compound according to Formula (I), and preferably Formula IA, such as 1,1,2,3-tetrachloropropene, is fed continuously through the catalyst bed at a fluorinating agent Formula (I) mole ratio, preferably HF/1,1,2,3-tetrachloropropene mole ratio, of about 4:1 to about 50:1 and preferably of about 4:1 to about 30:1 and more preferably of about 5:1 to about 20:1. The reaction is preferably carried out at a temperature of from about 30° C. to about 200° C. (preferably from about 50° C. to about 120° C.) and at a pressure of about 5 psia to about 200 psia (pounds per square inch absolute) (preferably from about 30 psia to about 175 psia). The catalyst may be supported on a substrate, such as on activated carbon, or may be unsupported or free-standing. It may be preferred in certain embodiments to activate the catalyst, such as with anhydrous hydrogen fluoride HF (hydrogen fluoride gas) and/or $Cl_2$ (chlorine gas) before use depending on the state of the catalyst. If desired, the catalyst can be kept activated by the continuous or batch addition of $Cl_2$ or a similar oxidizing agent.

Any vapor phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, molybdenum halide, an iron halide, a fluorinated chrome halide, a fluorinated chrome oxide or combinations thereof. Specific non-exclusive examples of vapor phase fluorination catalysts are $SbCl_3$, $SbCl_5$, $SbF_5$, $SnCl_4$, $TaCl_5$, $TiCl_4$, $FeCl_3$, $CrF_3$, $Cr_2O_3$ bulk or supported, and fluorinated $Cr_2O_3$ bulk or supported. Catalyst supports include carbon, alumina, fluorinated alumina, or aluminum fluoride, alkaline earth metal oxides, fluorinated alkaline earth metals, zinc oxide, zinc fluoride, tin oxide, and tin fluoride.

In general, the effluent from the fluorination reaction step, including any intermediate effluents that may be present in multi-stage reactor arrangements, may be processed to achieve desired degrees of separation and/or other processing. For example, in embodiments in which the reactor effluent comprises a compound of Formula (IB), such as HCFC-244bb, the effluent will generally also include HF and HCl. Some portion or substantially all of these components of the reaction product may be recovered from the reaction mixture via any separation or purification method known in the art such as neutralization and distillation, or in the reaction product may be fed in its entirety or in part, but without any separation of components, to the next step, i.e., dehydrohalogenation of the compound of Formula (IB). It is contemplated, therefore, that the desired compound of Formula (IB), such as HCFC-244bb, can be used in subpure form, or optionally in partially pure form or impure form with at least a portion of the effluent from the HCFC-244bb production step used as the feed to the dehydrohalogenation step.

In a continuous mode of operation, the desired compound(s) of Formula (IB), such as HCFC-244bb, and other reaction products, such as hydrogen chloride, are preferably continuously removed from the reactor.

II. Dehydrohalogenation of Formula (IB)

One preferred reaction step in accordance with the present invention may be described by those reactions in which the compound of Formula (IB) is dehydrohalogenated, preferably in certain embodiments dehydrochlorinated, to produce a compound of Formula (II). In certain preferred embodiments, the compound of Formula (IB) comprises a monochloro-tetrafluoro-propane, more preferably, 2-chloro-1,1,1,2-tetrafluoropropane (HCFC244bb), which is exposed to reaction conditions to produce a reaction product according to Formula (II), preferably comprising tetrafluoropropene, preferably 2,3,3,3-tetrafluoropropene HFO-1234yf.

In certain preferred embodiments, the stream containing the compound of Formula (IB) is preheated to a temperature of from about 150° C. to about 400° C., preferably about 350° C., and introduced into a reaction vessel, which is maintained at about the desired temperature, preferably from about 200° C. to about 700° C., more preferably from about 300° C. to about 700° C., more preferably from about 300° C. to about 450° C., and more preferably in certain embodiments from about 350° C. to about 450° C.

Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to about the desired reaction temperature.

Thus, it is contemplated that the dehydrohalogenation reaction step may be performed using a wide variety of process parameters and process conditions in view of the overall teachings contained herein. However, it is preferred in certain embodiments that this reaction step comprises a gas phase reaction, preferably in the presence of catalyst, and even more preferably in the presence of a fixed bed catalytic reactor in the vapor or gas phase.

In preferred embodiments, the catalyst is a carbon- and/or metal-based catalyst, preferably activated carbon (in bulk or supported form), a nickel-based catalyst (such as Ni-mesh), metal halides, halogenated metal oxides, neutral (or zero oxidation state) metal or metal alloy and combinations of these. Other catalysts and catalyst supports may be used, including palladium on carbon, palladium-based catalyst (including palladium on aluminum oxides), and it is expected that many other catalysts may be used depending on the requirements of particular embodiments in view of the teachings contained herein. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source. When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Of course, two or more any of these catalysts, or other catalysts not named here, may be used in combination.

The gas phase dehydrohalogenation reaction may be conducted, for example, by introducing a gaseous form of a compound of Formula (IB) into a suitable reaction vessel or reactor. Preferably the vessel is comprised of materials which are resistant to corrosion, especially to the corrosive effects of hydrogen chloride (to the extent that such material is formed under the dehydrohalogenation conditions) as mentioned above. Preferably the vapor phase reaction vessel contains catalyst, for example a fixed or fluid catalyst bed, packed with a suitable dehydrohalogenation catalyst, with suitable means to heat the reaction mixture to about the desired reaction temperature. The reaction vessel may employ single or multiple tubes packed with a dehydrohalogenation catalyst.

The compound of Formula (IB), preferably HCFC-244bb, may be introduced into the reactor either in pure form, partially purified form, or as portion or entirety of the reactor effluent from the preceding step. The compound of Formula (IB), such as HCFC-244bb, may optionally be fed with an inert gas diluent such as nitrogen, argon, or the like. In a preferred embodiment of the invention, the compound of Formula (IB), such as HCFC-244bb, is pre-vaporized or pre-heated prior to entering the reactor. Alternately, the compound of Formula (IB), such as HCFC-244bb, may be vaporized in whole or in part inside the reactor.

While it is contemplated that a wide variety of reaction temperatures may be used, depending on relevant factors such as the catalyst being used and the most desired reaction product, it is generally preferred that the reaction temperature for the dehydrohalogenation step is from about 100° C. to about 800° C., more preferably from about 150° C. to about 600° C., and even more preferably from about 200° C. to about 550° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum. The vacuum pressure can be from about 5 torr (0.0966 psig) to about 760 torr (14.69 psig).

In certain embodiments, an inert diluent gas, such as nitrogen, may be used in combination with the other reactor feed(s). When such a diluent is used, it is generally preferred that the compound of Formula (I), preferably Formula (IB), comprise from about 50% to greater than 99% by weight based on the combined weight of diluent and Formula (I) compound.

It is contemplated that the amount of catalyst use will vary depending on the particular parameters present in each embodiment. Contact time of the compound of Formula (IB), such as HCFC-244bb, with the catalyst in certain preferred embodiments ranges from about 0.5 seconds to about 120 seconds, however, longer or shorter times can be used.

Preferably in such dehydrofluorination embodiments as described in this section, the conversion of the Formula (IB) compound is at least about 10%, more preferably at least about 20%, and even more preferably at least about 30%. Preferably in such embodiments, the selectivity to compound of Formula (II), preferably HFO-1234yf, is at least about 70%, more preferably at least about 85% and more preferably at least about 95%.

In certain preferred embodiments, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days.

In general, the effluent from the dehydrohalogenation reaction step, including any intermediate effluents that may be present in multi-stage reactor arrangements, may be processed to achieve desired degrees of separation and/or other processing. For example, in embodiments in which the reactor effluent comprises a compound of Formula II, such as HFO-1234yf, the effluent will generally also include HCl and unreacted compound of the Formula (IB). Some portion or substantially all of these components of the reaction product may be recovered from the reaction mixture via any separation or purification method known in the art such as neutralization and distillation. It is expected that unreacted compound of the Formula (IB) could be recycled, completely or partially, to improve the overall yield of the desired $CF_3CF=CH_2$ (HFO-1234yf). Optionally but preferably, hydrogen chloride is then recovered from the result of the dehydrochlorination reaction. Recovering of hydrogen chloride is preferably conducted by conventional distillation where it is removed from the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

In an alternate embodiment of the invention, dehydrohalogenation of HCFC-244bb can also be accomplished by reacting it with a strong caustic solution that includes, but is not limited to KOH, NaOH, $Ca(OH)_2$ and CaO at an elevated temperature. In this case, the strength of the caustic solution is preferably from about 2 wt % to about 100 wt %, more preferably from about 5 wt % to about 90 wt % and most preferably from about 10 wt % to about 80 wt %. The caustic: Formula (IB) mole ration, preferably the caustic:HCFC-244bb mole ratio, preferably ranges from about 1:1 to about 2:1; more preferably from about 1.1:1 to about 1.5:1 and even more preferably from about 1.2:1 to about 1.4:1. The reaction may be conducted at a temperature of from about 20° C. to about 100° C., more preferably from about 30° C. to about 90° C. and even more preferably from about 40° C. to about 80° C. As above, the reaction may be conducted at atmospheric pressure, super-atmospheric pressure or under vacuum. The vacuum pressure can be from about 5 torr (0.0966 psig) to about 760 ton (14.69 psig). In addition, a solvent or phase transfer catalyst such as Aliquat 336 may optionally be used to help dissolve the organic compounds in the caustic solution. This optional step may be conducted using solvents that are well known in the art for said purpose. Thereafter, the Formula (II) compound, preferably HFO-1234yf, may be recovered from the reaction product mixture comprised of unreacted starting materials and by-products by any means known in the art, such as by extraction and preferably distillation. In certain preferred embodiments, the mixture of HFO-1234yf and any by-products are passed through a distillation column. For example, the distillation may be preferably conducted in a standard distillation column at atmospheric pressure, super-atmospheric pressure or a vacuum. Preferably the pressure is less than about 300 psig, preferably less than about 150 psig and most preferably less than 100 psig. The pressure of the distillation column inherently determines the distillation operating temperature.

Preferably in such dehydrofluorination embodiments as described in this section, the conversion of the Formula (IB) compound is at least about 60%, more preferably at least about 75%, and even more preferably at least about 90%. Preferably in such embodiments, the selectivity to compound of Formula (II), preferably HFO-1234yf, is at least about 70%, more preferably at least about 85% and more preferably at least about 95%.

EXAMPLES

Additional features of the present invention are provided in the following examples, which should not be construed as limiting the claims in any way.

Example 1

Continuous Liquid Phase Preparation of $CF_3CFClCH_3$ (HCFC-244bb) from $CCl_2=CClCH_2Cl$ A 1.5" 1D×24" long PFA-lined pipe was filled with 550 grams of antimony pentachloride liquid phase fluorination catalyst. This was heated to approximately 95° C., and then fluorinated with 5 moles of anhydrous hydrogen fluoride. Then a continuous feed of 1,1,2,3-tetrachloropropenewas begun, simultaneous with continuous feed of HF. These feeds were maintained in a mole ratio of HF to 1,1,2,3-TCP of about 17:1, with a residence time of about 1 second. The reactor was maintained at about 96° C. Volatiles from the run were collected in a dry ice cold trap, analyzed, and found to produce a nearly total conversion of the 1,1,2,3-tetrachloropropene, with selectivity of about 22% to 2-chloro-1,1,1,2-tetrafluoropropane (244bb), and selectivity of about 33% to 2-chloro-3,3,3-trifluoropropene (1233xf), and selectivity of about 27% to precursor 2,3-dichloro-3,3-difluoropropene (1232xf) and selectivity of >12% to overchlorinated species 1223xd attributed to excess $Cl_2$ feed to the reactor to keep the catalyst active.

Example 2

Continuous Liquid Phase Preparation of $CF_3CFClCH_3$ (HCFC-244bb) from $CCl_2=CClCH_2Cl$ Example 1 was repeated except 515 grams of antimony pentachloride was used, mole ratio of HF to 1,1,2,3-TCP is about 30:1, and the residence time was about 2.1 seconds, and the pressure in the reactor was allowed to build to about 14 psig. Volatiles from the run were collected in a dry ice cold trap, analyzed, and found to produce a nearly total conversion of the 1,1,2,3-tetrachloropropene, with selectivity of about 16.7% to 2-chloro-1,1,1,2-tetrafluoropropane (244bb), and selectivity of about 33.5% to precursor 2-chloro-3,3,3-trifluoropropene (1233xf), and selectivity of about 34.6% to precursor 2,3-dichloro-3,3-difluoropropene (1232), and selectivity of >10.0% to overchlorinated species 1223xd attributed to excess $Cl_2$ feed to the reactor to keep the catalyst active.

Example 3

Batch Liquid Phase Preparation of $CF_3CFClCH_3$ (HCFC-244bb) from $CCl_2=CClCH_2Cl$ To a 1 Liter monel Parr reactor is added 83 grams of $SbCl_5$ and 300 grams of HF. After heating to 85° C., the HCl and noncondensibles are vented to a DIT. Then 50 grams of $CCl_2=CClCH_2Cl$ are quickly added. The mole % ratio of $SbCl_5$ to $CCl_2=CClCH_2Cl$ is 50/50. There is an immediate exotherm and the temperature rises to 97° C. almost instantaneously. The variac controlling the heater is turned off and the reaction held between 97 and 87° C. for an hour. The pressure rises to 400 psig and levels off. A vapor sample is taken into gas bags containing DI $H_2O$ (to absorb the HF and HCl prior to analysis). A GC of the gas bag sample shows 53.5 GC area % 244bb, 1.46 GC area % overfluorinated species HFC245cb, 6.6 GC area % overchlorinated species 1223xd along with 1233xf precursor, 1232xf precursor, and some C6 compounds that may be dimers. The conversion of $CCl_2=CClCH_2Cl$ on a GC area % basis is 100%.

Example 4

Conversion of $CF_3CFClCH_3$ (HCFC-244bb) to $CF_3CF=CH_2$ in Continuous Gas-Phase This example illustrates the continuous vapor phase dehydrochlorination reaction of 2-chloro-1,1,1,2-tetrafluoropropane (244bb)→2,3,3,3-tetrafluoropropene (1234yf)+HCl. The dehydrochlorination catalyst is 10 wt % CsCl/90 wt % MgF$_2$.

Conversion of HCFC-244bb into HFO-1234yf was performed using Monel reactor (ID 2 inch, length 32 inch) equipped with a Monel preheater (ID 1 inch, length 32 inch) which was filled with Nickel mesh to enhance heat transfer. The reactor is filled with 2.0 L of pelletized 10 wt % CsCl/90 wt % MgF$_2$ dehydrochlorination catalyst. Nickel mesh is placed at the top and at the bottom of reactor to support the catalyst. Multi-point thermocouple is inserted at the center of the reactor. The catalyst is pretreated in dry N2 flow for 6 hours at the temperature of 480° C. Then the feed with the composition 95 GC % 244bb/3.1 GC % 1233xf/0.35 GC % 245cb is introduced into the reactor at the rate of 1.0 lb/hr. The feed is vaporized prior entering the reactor preheater. The bottoms of the distillation column is discharged and recycled into the reactor. The feed rate is maintained constant at 1.0 lbs/hr and both temperature and pressure are varied. Temperature gradient throughout the reactor is within about 3-5° C. The productivity of the catalyst is estimated at 3-6 lbs/hr/ft$^3$. The highest productivity is observed at 470° C. and 45 psig, and the lowest productivity is observed at 480° C. and 3 psig pressure. The reaction products are fed into the caustic scrubber to remove HCl by-product. Then the product stream is passed through a column filled with desiccant to remove residual moisture. Oil-less compressor was used to feed crude product into the distillation column that was maintained at 30-45 psig pressure. Distillation was performed in a continuous mode and the take-off rate was equal to the rate of production of HFO-1234yf in the reactor. The purity of distilled 1234yf is 99.9 GC %+. GC analysis of the distillate shows presence of light impurities with a ppm level of heavy impurities.

The following conversions and selectivities are achieved:
  480° C. at 3 psig—244bb conversion ~30%, Selectivity to 1234yf ~97%
  480° C. at 20 psig—244bb conversion ~47%, Selectivity to 1234yf ~96%
  470° C. at 20 psig—244bb conversion ~36%, Selectivity to 1234yf ~97%
  470° C. at 45 psig—244bb conversion ~53%, Selectivity to 1234yf ~96%
  460° C. at 45 psig—244bb conversion ~38%, Selectivity to 1234yf ~98%

Reaction Data

Conditions: Feed 95 GC % 244bb/3.1 GC % 1233xf/0.35 GC % 245cb; 2.0 L of 10 wt % CsCl/90 wt % MgF$_2$ catalyst; 1.0 lb/hr feed rate.

| Time on-stream (hrs.) | conversion of 244bb (%) | Selectivity to 1234yf (%) | Temperature (° C.) | Pressure (psig) |
| --- | --- | --- | --- | --- |
| 0.25 | 93.30 | 82.42 | 484.30 | 3.00 |
| 0.80 | 67.61 | 90.38 | 489.00 | 3.90 |
| 1.43 | 47.78 | 94.14 | 479.80 | 3.50 |
| 2.27 | 31.98 | 97.34 | 479.80 | 3.40 |
| 3.32 | 29.36 | 97.70 | 478.80 | 3.80 |
| 4.32 | 26.24 | 97.56 | 478.70 | 2.80 |
| 5.23 | 28.45 | 97.88 | 480.30 | 2.90 |
| 6.20 | 30.53 | 98.01 | 480.30 | 3.20 |
| 6.80 | 30.91 | 98.13 | 478.40 | 3.30 |
| 7.37 | 28.36 | 97.88 | 478.80 | 2.90 |
| 7.93 | 29.01 | 97.84 | 479.30 | 3.10 |
| 8.48 | 29.95 | 97.91 | 478.30 | 3.30 |
| 9.05 | 26.61 | 96.76 | 479.60 | 2.70 |
| 9.62 | 27.98 | 96.12 | 476.80 | 2.90 |
| 10.20 | 28.84 | 96.66 | 480.20 | 3.00 |
| 10.70 | 29.70 | 97.16 | 480.50 | 3.10 |
| 11.22 | 29.30 | 97.62 | 480.30 | 3.30 |
| 11.72 | 30.47 | 97.65 | 480.70 | 3.30 |
| 12.25 | 29.57 | 97.59 | 480.30 | 3.30 |
| 12.75 | 29.83 | 97.92 | 480.00 | 3.50 |
| 13.27 | 30.10 | 98.23 | 479.60 | 2.80 |
| 13.78 | 28.73 | 97.02 | 480.10 | 2.80 |
| 14.28 | 29.54 | 97.31 | 480.80 | 2.90 |
| 14.80 | 29.95 | 98.05 | 479.80 | 2.90 |
| 15.30 | 29.71 | 97.98 | 480.60 | 3.00 |
| 15.80 | 30.50 | 98.14 | 480.80 | 2.90 |
| 16.32 | 30.68 | 97.96 | 481.50 | 3.10 |
| 16.83 | 32.21 | 97.79 | 482.50 | 3.10 |
| 17.35 | 30.37 | 97.68 | 478.00 | 3.20 |
| 17.85 | 27.67 | 97.18 | 479.20 | 3.30 |
| 18.40 | 28.06 | 96.50 | 477.50 | 3.20 |
| 18.95 | 27.84 | 96.58 | 478.20 | 3.40 |
| 19.50 | 28.85 | 96.66 | 482.30 | 3.40 |
| 20.18 | 32.52 | 97.55 | 480.00 | 3.40 |
| 20.87 | 29.15 | 97.47 | 480.10 | 3.20 |
| 22.90 | 64.16 | 97.20 | 478.90 | 17.40 |
| 23.65 | 47.32 | 96.23 | 477.80 | 17.50 |
| 24.32 | 47.80 | 96.81 | 478.60 | 17.00 |
| 25.00 | 47.45 | 96.83 | 479.40 | 16.90 |
| 26.02 | 47.10 | 96.84 | 479.50 | 18.50 |
| 26.78 | 46.99 | 97.34 | 478.60 | 20.00 |
| 27.38 | 48.61 | 97.45 | 478.80 | 20.00 |
| 28.22 | 47.00 | 97.41 | 477.80 | 20.00 |
| 28.93 | 48.53 | 96.40 | 480.00 | 20.00 |
| 29.63 | 46.61 | 96.10 | 477.70 | 20.00 |
| 30.23 | 49.28 | 96.14 | 480.80 | 20.00 |
| 30.83 | 44.30 | 96.11 | 477.70 | 20.00 |
| 31.45 | 48.53 | 96.18 | 479.50 | 20.00 |
| 32.05 | 45.03 | 97.45 | 477.70 | 20.00 |
| 32.72 | 48.94 | 97.09 | 480.10 | 20.00 |
| 33.30 | 45.10 | 96.24 | 478.00 | 20.00 |
| 33.83 | 46.72 | 96.25 | 479.70 | 20.00 |
| 34.37 | 49.04 | 96.21 | 479.30 | 20.00 |
| 34.90 | 46.86 | 96.34 | 477.80 | 20.00 |
| 35.42 | 41.57 | 97.52 | 474.60 | 20.00 |
| 35.95 | 38.83 | 97.44 | 469.40 | 20.00 |
| 36.48 | 31.20 | 97.45 | 468.40 | 20.00 |
| 37.02 | 34.86 | 96.45 | 470.10 | 20.00 |
| 37.55 | 35.41 | 96.44 | 470.20 | 20.00 |
| 38.07 | 37.17 | 97.71 | 469.90 | 20.00 |
| 38.63 | 36.72 | 97.31 | 471.10 | 20.00 |
| 39.15 | 36.66 | 97.68 | 470.00 | 20.00 |
| 39.67 | 37.41 | 97.85 | 470.80 | 20.00 |
| 40.20 | 36.43 | 97.86 | 469.40 | 20.00 |
| 40.73 | 36.10 | 97.98 | 469.20 | 20.00 |
| 41.27 | 35.34 | 97.97 | 470.50 | 20.00 |
| 42.05 | 37.63 | 96.08 | 472.00 | 20.00 |
| 42.57 | 38.60 | 97.20 | 470.30 | 20.00 |
| 43.12 | 57.72 | 96.75 | 469.60 | 45.00 |
| 43.65 | 53.72 | 95.42 | 467.10 | 45.00 |
| 44.17 | 51.28 | 94.83 | 468.70 | 45.00 |
| 44.68 | 51.60 | 96.39 | 467.50 | 45.00 |
| 45.20 | 52.52 | 96.36 | 469.80 | 45.00 |
| 45.72 | 53.43 | 96.65 | 468.90 | 45.00 |
| 46.77 | 51.14 | 95.44 | 468.50 | 45.00 |
| 48.15 | 53.38 | 97.23 | 470.70 | 45.00 |
| 49.32 | 54.53 | 97.21 | 470.90 | 45.00 |
| 50.88 | 51.94 | 97.21 | 469.40 | 45.00 |
| 52.35 | 39.24 | 97.70 | 459.60 | 45.00 |
| 53.75 | 39.15 | 97.19 | 459.30 | 45.00 |
| 55.03 | 38.45 | 97.63 | 458.30 | 45.00 |
| 56.57 | 37.19 | 97.61 | 457.50 | 45.00 |
| 57.85 | 37.44 | 97.88 | 458.90 | 45.00 |
| 58.93 | 38.18 | 97.91 | 458.80 | 45.00 |
| 59.98 | 37.98 | 98.04 | 460.10 | 45.00 |
| 61.05 | 39.77 | 97.43 | 463.00 | 45.00 |
| 62.10 | 42.11 | 97.92 | 462.20 | 45.00 |
| 63.20 | 41.11 | 97.74 | 459.10 | 45.00 |

-continued

| Time on-stream (hrs.) | conversion of 244bb (%) | Selectivity to 1234yf (%) | Temperature (° C.) | Pressure (psig) |
|---|---|---|---|---|
| 64.27 | 39.64 | 98.05 | 460.60 | 45.00 |
| 65.32 | 40.98 | 97.70 | 461.40 | 45.00 |

What is claimed is:

1. A process for making a tetrafluoropropene, comprising: dehydrohalogenating 2-chloro-1,1,1,2-tetrafluoropropane (HCFC-244bb) in the presence of a caustic agent.

2. The process of claim 1 wherein the tetrafluoropropene is 2,3,3,3-tetrafluoropropene.

3. The process of claim 1 wherein the caustic agent is at least one agent selected from the group consisting of KOH, NaOH, Ca(OH)$_2$, and CaO.

4. The process of claim 3 wherein the caustic agent is KOH.

5. The process of claim 1 wherein the caustic agent is provided in a solution having a caustic agent strength of between about 2 wt % and about 100 wt. %.

6. The process of claim 1 wherein the caustic agent is provided in a solution having a caustic agent strength of between about 5 wt % and about 90 wt. %.

7. The process of claim 1 wherein the caustic agent is provided in a solution having a caustic agent strength of between about 10 wt % and about 80 wt. %.

8. The process of claim 1 wherein a mole ratio of the caustic agent:HCFC-244bb is from about 1:1 to about 2:1.

9. The process of claim 1 wherein a mole ratio of caustic agent:HCFC-244bb is from about 1.1:1 to about 1.5:1.

10. The process of claim 1 wherein a mole ratio of caustic agent:HCFC-244bb is from about 1.2:1 to about 1.4:1.

11. The process of claim 1 wherein the dehydrohalogenating step is conducted at a temperature from about 20° C. to about 100° C.

12. The process of claim 1 wherein the dehydrohalogenating step is conducted at a temperature from about 30° C. to about 90° C.

13. The process of claim 1 wherein the dehydrohalogenating step is conducted at a temperature from about 40° C. to about 80° C.

14. The process of claim 1 wherein a reaction pressure of the process ranges from atmospheric pressure, super-atmospheric pressure and sub-atmospheric pressure.

15. The process of claim 1 further comprising a phase transfer catalyst.

16. The process of claim 1 further comprising recovering the tetrafluoropropene.

* * * * *